(12) United States Patent
Claibourn et al.

(10) Patent No.: US 6,387,705 B1
(45) Date of Patent: May 14, 2002

(54) ALKYLATION PROCESS USING REFRACTIVE INDEX ANALYZER

(75) Inventors: Terry Valdene Claibourn, Saint Charles, MO (US); Phillip Jack Hamilton, Granite City, IL (US)

(73) Assignee: Equilone Enterprises, LLC, Houston, TX (US)

( * ) Notice: Subject to any disclaimer, the term of this patent is extended or adjusted under 35 U.S.C. 154(b) by 0 days.

(21) Appl. No.: 09/576,456

(22) Filed: May 23, 2000

Related U.S. Application Data

(60) Provisional application No. 60/201,127, filed on May 2, 2000.

(51) Int. Cl.[7] .......................... G01N 21/35; G01N 21/59
(52) U.S. Cl. ........................ 436/55; 436/40; 436/60; 436/139; 436/171; 250/339.05; 250/338.1; 250/339.11
(58) Field of Search ...................... 436/55, 40; 585/446, 585/462, 464, 459, 466, 709, 723, 725, 726, 727, 730, 331; 73/61.48; 524/297; 250/339.05

(56) References Cited

U.S. PATENT DOCUMENTS

| | | | |
|---|---|---|---|
| 3,653,835 A | | 4/1972 | Brandel ........................ 23/230 |
| 3,917,557 A | * | 11/1975 | Kirk, Jr. et al. ............. 524/297 |
| 3,935,097 A | | 1/1976 | Roof ............................ 210/31 |
| 4,009,998 A | | 3/1977 | Benningfield, Jr. .......... 23/230 |
| 4,571,075 A | | 2/1986 | Kamrat ........................ 356/136 |
| 4,776,697 A | | 10/1988 | Kamrat ........................ 356/336 |
| 5,407,830 A | * | 4/1995 | Altman et al. ................. 436/55 |
| 5,583,049 A | * | 12/1996 | Altman et al. ................. 436/55 |
| 5,681,749 A | | 10/1997 | Ramamoorthy .............. 436/55 |
| 5,708,270 A | * | 1/1998 | Chimenti et al. ....... 250/339.05 |
| 6,035,705 A | * | 3/2000 | Alexander ................... 73/61.48 |
| 6,096,553 A | * | 8/2000 | Heald et al. ................... 436/40 |
| 6,228,650 B1 | * | 5/2001 | Moore et al. ................. 436/55 |

\* cited by examiner

Primary Examiner—Robert J. Warden, Sr.
Assistant Examiner—Brian Sines
(74) Attorney, Agent, or Firm—Locke Liddell & Sapp LLP

(57) ABSTRACT

An alkylation process that employs a refractive index analyzer to monitor, control, and/or determine acid catalyst strength before, during, or after the alkylation reaction. In a preferred embodiment, the invention relates to the alkylation of an olefinic feedstock with a sulfuric acid catalyst. The acid typically enters the alkylation reactor train at between from about 92 to about 98 weight percent strength. The concentration of acid is controlled and maintained by monitoring the refractive index of the acid in the product mixture comprising alkylate, mineral acid, water, and red oil. At least one online analyzer using a refractometer prism sensor producing real-time measurements of the refractive index of the solution may be compared to the results of manual laboratory tests on the acid strength of the catalyst using manual sample analyses or titration methods. Periodically, after calibration of the system, samples may be taken to verify the precision of the online analyzer, if desired. In a preferred embodiment, at least one sensor is connected to at least one transmitter and is capable of providing information related to the concentration of alkylation catalyst in the mixture such that the concentration level of acid in the mixture may be monitored and maintained.

20 Claims, 6 Drawing Sheets

ALKYLATION PROCESS USING REFRACTIVE INDEX ANALYZER

This application claims benefit under 35 U.S.C. §120 to Provisional Application No. 60/201,127 filed on May 2, 2000.

FIELD OF THE INVENTION

The present invention relates to a method of monitoring acid strength during alkylation of an olefinic feedstream by use of at least one refractive index analyzer. In addition, the invention relates to an alkylation process using at least one refractive index analyzer to generate real-time concentration readings. The invention further relates to a method of determining and controlling acid concentration during an alkylation process.

BACKGROUND OF THE INVENTION

In light of the curtailment in the use of tetraethyl lead as an octane-improving additive for gasoline, the production of unleaded gasoline has increased as well as the octane number specification of all grades of gasoline. Additionally, recent reformulated gasoline specifications require a reduction in both the Reid Vapor Pressure ("RVP") and olefin content. Alkylate is a low vapor pressure, high-octane gasoline blending component containing essentially no olefins. Thus, alkylate helps refiners meet the new reduced RVP and reduced olefin content specifications. Additionally, alkylate burns cleanly, resulting in lower levels of undesired emissions from gasoline engines.

Alkylation, a well-known refinery process for converting light, gaseous olefins into high-octane gasoline components, involves the addition of an alkyl group to an organic molecule. In alkylation, an isoparaffin is typically reacted with an olefinic hydrocarbon feed to provide an isoparaffin of higher molecular weight. Generally, the alkylation of isoparaffins with olefins is accomplished by contacting the reactants with an acid catalyst such as hydrogen fluoride or sulfuric acid, settling the mixture to separate the catalyst from hydrocarbons, and further separating the hydrocarbons, usually by fractionation to recover the alkylated product. The alkylation reaction product is referred to as "alkylate", and it preferably contains (in order to render the highest quality gasoline blending stock) branched chain hydrocarbons having five to sixteen carbon atoms, with the exact composition depending upon the isoparaffin and olefinic hydrocarbon feed used, as well as process conditions.

The olefinic hydrocarbon feed generally comes from a catalytic cracker and contains olefins, paraffins, and isoparaffins in the $C_3$–$C_5$ range. Common impurities present in the feed are mercaptan sulfur, diolefins, and free water. Diolefins, such as butadiene, present in the olefinic hydrocarbon feedstream, are known to consume the acid catalyst at rapid rates. The result is the formation of acid-soluble hydrocarbons, known as red oil or acid-soluble oil (ASO) in the acid phase and a lowering of the quality of the alkylate octane.

Under optimum conditions in commercial alkylation reactors, sulfuric acid usually enters the reactor at 98% weight strength and exits at 89% weight strength. Each percent above the 89% target that the acid exits the reactor represents a 10% waste in total acid consumption. In the alkylation of isoparaffins and olefins with a strong mineral acid such as sulfuric acid, it is critically important to be able to recycle the used or spent acid back to the reactor. This used or spent acid is comprised of three components—acid, water, and red oil or ASO. The latter accumulates in the acid phase, thereby lowering the acid strength of the catalyst. The composition of red oil in an alkylation unit varies depending upon the feed composition and reaction conditions. Red oil is soluble in the acid catalyst and may be chemically bound by the strong acid catalyst. It is important to know the acid content of the recycle acid in order to determine the amount of fresh acid needed to bring the mixture of fresh and recycle acid to the desired concentration of acid in the alkylation reactor.

If the acid strength within the alkylation reactor falls below about 86%, "acid runaway" becomes eminent, where the acid strength depletes so rapidly that the feedstock into the unit must be cut off. It is then necessary to increase the flow of fresh acid in order to halt the degradation. If an unusually rapid drop in acidity is detected before the acidity drops below the safe minimum acidity, the acidity can usually be brought back to a safe level by increasing the fresh acid feed.

Previously, operators relied on chemical laboratories for acid titration data to determine acid catalyst strength. In so doing, they were gambling on the possibility that the acidity could not be raised to a point at which the acid could act as catalyst. Furthermore, such methods were not responsive to short-swing upsets during operations.

Several attempts have been made to measure acid strength on physical properties of the catalyst. For example, U.S. Pat. No. 3,653,835 teaches measuring the specific gravity of a sample of spent sulfuric acid as a means of measuring the concentration of acid. U.S. Pat. No. 3,935,097 describes a system directed to high-pressure liquid chromatography for separation of acid and water. Further U.S. Pat. No. 4,009,998 discloses a method for measuring the concentration of acid by electrical conductivity. Still further, some operators have used the viscosity of the spent acid to correlate the acidity of the system acid. Such methods have seen limited success primarily because they use an indirect means to correlate the acidity. Furthermore, the presence of red oil in varying amounts can adversely influence the measurement. All of these methods are based on sampling and do not offer the alkylation plant operator the ability to maintain a continuous control of the acidity of the alkylation catalyst and thus control of the quality of product.

Continuous on-line analysis of acid strength by near-infrared spectrophotometry is disclosed in U.S. Pat. No. 5,681,749. Such means, however, requires advanced training and is relatively expensive to maintain. Other methods have been employed in an attempt to achieve in-situ determination of the acidity of acid-water solutions. For example, on-line continuous acidity analysis has been documented by monitoring velocity of sound in the flowing acid stream. This system is dependent upon the density of the medium and is accurate only for certain acid-water solutions that do not contain red oil. Other techniques have been utilized to measure on-line acidity strength include nuclear magnetic resonance ("NMR").

All of these techniques present serious limitations including limited accuracy, complex modeling, and sample conditioning requirements contributing to application complexity, high installation costs, and maintenance/reliability concerns. In addition, they fall short of meeting an operator's need to accurately monitor and control the acid strength in commercial operations. In commercial plants, the amount of red oil content of acid typically varies over a wide range. Thus, it is desirable to have a method that can reliably measure the acid strength regardless of the variations in the red oil content.

It is an object of this invention to provide a method for the alkylation operator to continuously monitor on-line and control with confidence the acid strength in a commercial hydrocarbon conversion process.

In particular, it is an object of the invention to provide a method for use by the alkylation plant operator to adequately maintain continuous control of the acidity of the alkylation catalyst and therefore control the product octane quality.

It is further an object of this invention to provide a reliable method of measuring the acid strength in a mixture comprising a mineral acid, water and red oil in a hydrocarbon conversion process by a continuous in-line technique to enable operators to make adjustments to their fresh acid addition rate and spent acid purging rate, thereby improving product quality.

It is also an object of this invention to provide a method for determining the concentration of acid by an on-line analyzer which affords greater accuracy and which is easier to use than the on-line analyzers of the prior art.

SUMMARY OF THE INVENTION

The invention relates to an alkylation process employing a refractive index analyzer to monitor, control and/or determine acid catalyst strength during alkylation of an olefinic feedstream. In a preferred embodiment, the invention relates to the alkylation of a hydrocarbon mixture comprising olefins and paraffins with a sulfuric acid catalyst. The acid enters the akylation reactor train at approximately 98% weight strength and exits at approximately 89% weight strength. The concentration of acid is controlled and maintained by monitoring the refractive index of the acid in the product mixture, most preferably comprising mineral acid, water and red oil. Online analyzer results may be compared to the results of manual laboratory tests on the acid strength of the catalyst using manual sample analyses or titration methods. Periodically, after calibration of the system, samples may be taken to verify the precision of the online analyzer, if desired.

The method of the invention permits a determination of alkylation catalyst with a precision that is comparable to that which can be achieved with large bench-top, non-portable instruments. Moreover, in a preferred embodiment, the present invention may further provide a direct readout display of the acid concentration.

The refractive index analyzer for use in the method of the invention includes a refractive index sensor with a refractometer prism having a measuring surface which contacts the outer surface of pipe or similar conduit through which passes the product mixture of alkylate, mineral acid, water and red oil. Furthermore, the sensor preferably includes a substantially monochromatic light source disposed with the sensor such that the light source, upon activation, is capable of directing a light beam through the conduit or is redirected via at least one mirror. In so doing, light enters the light entrance side of the prism and at least a portion of the light is refracted from the measuring surface of the prism into the sample medium and at least a portion of the light is reflected back through the exit side of the prism to a photodetector. The portion of beam reflected to the photodetector is dependent on the boundary formed by critical angle $\Phi_{CRIT}$ at the measuring surface. This angle is dependent on refractive indices of the prism and the liquid in contact with the measuring surface. The refractive index of the mixture in contact with the measuring surface is dependent on the percentage concentration of alkylation catalyst in the liquid and is collected by an image detector and image digitizer capable of generating a "drift-free" digital image signal that may be displayed and/or processed after being transmitted to at least one processor by at least one transmitter. Ultimately, the percentage concentration of the constituent may be visually displayed and monitored.

The sensor, may further be used in conjunction with other sensors that are linked to transmitters such that the concentration of acid in the product mixture may be monitored at least one location within a plant, refinery, or similar structure.

In a preferred embodiment, the alkylation catalyst is sulfuric acid in which the sensor and transmitter provides information related to the concentration of the sulfuric acid within the hydrocarbon mixture such that the concentration of sulfuric acid may be monitored and maintained at the requisite level.

DETAILED DESCRIPTION OF PREFERRED EMBODIMENTS

Figure 1:
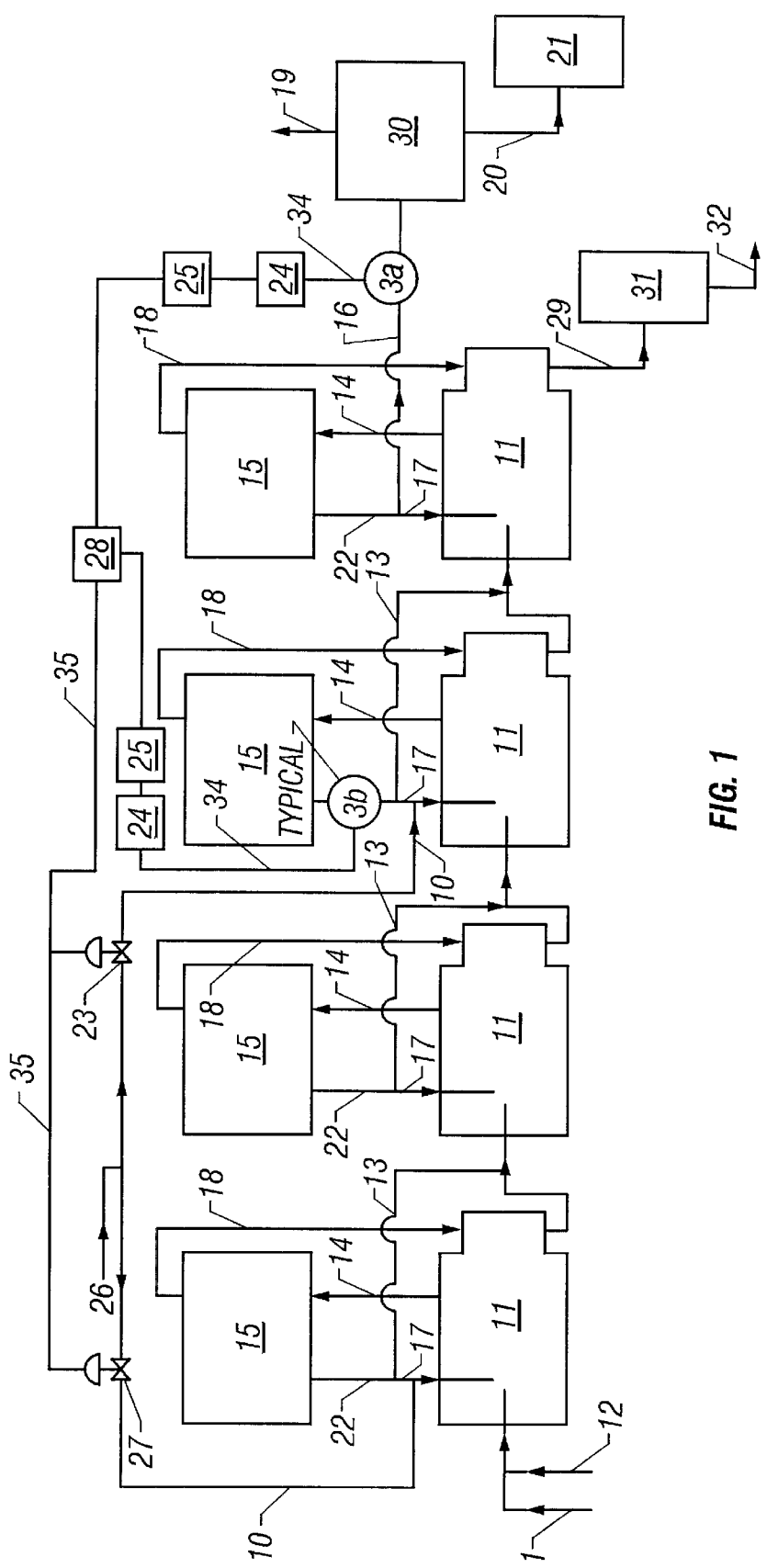
FIG. 1 is a schematic view of a preferred embodiment of the alkylation method of the invention depicting the refractive index analyzer.

The method of the invention relates to alkylation of an olefinic feedstream by use of a refractive index analyzer that serves to monitor, control as well as determine the acid concentration during the alkylation process. As a result, the inventive process reduces acid consumption. As used herein, "acid consumption" relates to the dilution of the acid catalyst by acid soluble oils formed by undesirable side reactions. Additionally, formation of stable intermediates, such as sulfate esters when utilizing sulfuric acid catalyst, also dilute the catalyst causing an apparent acid consumption increase. "Acid strength" as used herein refers to the concentration of the acid catalyst expressed in weight percent as determined by titration with standardized sodium hydroxide.

In the method of the invention, an olefinic feed is alkylated with an alkane, typically an isoparaffin, in the presence of a suitable catalyst. The desired resulting product is an alkylate. The olefin feed generally includes olefins having two or more carbon atoms, preferably having three to five carbon atoms. The isoparaffin typically has four or more carbon atoms. Although any suitable isoparaffin that can be alkylated to provide the desired alkylate product may be utilized, it is preferred to utilize isobutane as the isoparaffin.

The alkylation temperature and pressure utilized in the method of the invention is generally selected to yield the desired alkylation products without undue detrimental effects upon the catalyst or alkylation reactants. Generally, the alkylation temperature utilized in the present invention is in the range of about −60° F. to about 1000° F. Preferably, the alkylation temperature utilized in the present invention is in the range of about −40° F. to about 200° F., more preferably in the range of about 35° F. to about 200° F., and most preferably in the range of about 35° F. to about 125° F. The upper limit on the alkylation temperature is generally selected to avoid undue temperature degradation of the catalyst and to keep the catalyst in the desired state. For example, with sulfuric acid catalysts, the alkylation temperature is most preferably in the range of about 40° F. to about 60° F. and generally requires some type of refrigeration, while the most preferable alkylation temperature when utilizing hydrogen fluoride catalysts is in the range of about 85° F. to about 115° F., which can generally be maintained utilizing cooling water. It is observed that at lower temperatures the rate of reaction is generally slower, and at higher temperatures, some cracking, polymerization and carbon formation occurs. The alkylation temperature utilized will generally also be influenced by economy of equipment and operating costs.

The alkylation pressure utilized in the present invention is generally selected to maintain at least a portion of, and preferably a majority of, the hydrocarbon reactants in a liquid phase. Generally, the reaction pressure is in the range of about atmospheric to about 5000 PSI or more, preferably in the range of about 45 PSI to about 1000 PSI, and most preferably in the range of about 45 PSI to about 250 PSI.

Contact times for hydrocarbon reactants in the alkylation reactor should be sufficient to provide for essentially complete conversion of the olefin feed. Although the residence time of the reactants in the reactor can vary widely depending upon the process variables, the residence time is generally in the range of about 0.01 minutes to about 100 minutes. Preferably, the residence time is in the range of about 0.1 minutes to about 30 minutes, and more preferably in the range of about 1 minutes to about 20 minutes, and most preferably in the range of about 5 minutes to about 20 minutes.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. Usually a sufficient level of agitation is provided to maintain intimate contact between the two liquid phases. High levels of agitation are generally more important for sulfuric acid alkylation than for HF alkylation. The agitation is generally provided utilizing baffling, positioning of the impeller and by recycle streams.

After a sufficient time, the alkylate can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

In the practice of the alkylation process of the present invention, the precise process steps and process conditions will vary somewhat depending upon the catalyst system utilized, the alkylate product desired, available equipment, process economics and other factors. It is anticipated that any suitable catalyst may be utilized, including liquid, solid or any other type of catalyst.

For the present invention the alkylation is generally carried out by contacting the catalyst and the reacting hydrocarbons in a reactor under closely controlled conditions. Alkylation reactions are very exothermic and require cooling to remove the heat of reaction from the reactor. Reactor systems useful in the practice of the present invention include time-tank or pipe reactors, contactor reactors, cascade reactors, gravity reactors, solid catalyst reactors, and other types of alkylation reactors known to those of skill in the art.

The alkylation catalyst utilized in the present alkylation invention may be any catalyst that will catalytically effect the reaction of the isoparaffins and olefins. Suitable catalysts include strong acid catalysts such as hydrofluoric acid, sulfuric acid, phosphoric acid, mixtures of sulfuric and phosphoric acids, metal halides such as aluminum chloride or aluminum bromide, certain complexes of aluminum chloride and sulfuric acid, and the like.

Acid strength of the catalyst utilized in the present invention is generally maintained high enough to avoid dilution of the acid catalyst but low enough to avoid excessive side reactions. For example, the range of useful strengths of sulfuric acid is generally in the range of about 86 to about 99 weight percent.

The volume ratio of catalyst to total hydrocarbons is generally in the range of about 10:1 to about 1:10, and preferably in the range of about 10:1 to about 1:2.

The major processing steps of a commercial alkylation unit, and also various preferred monitoring points for the practice of this embodiment are outlined in FIG. 1. Referring to FIG. 1, there is illustrated diagrammatically a specific form of alkylation process for the purpose of illustrating the use of the present invention. In operation, a large stream of hydrocarbons undergoes alkylation in the presence of an acid catalyst such as sulfuric acid. The fresh olefinic feed 1, such as an isobutane, enters the first reactor 11, along with recycle feed in line 12 coming from a deisobutanizer, and acid from line 10. The reaction product, an emulsion containing alkylate, acid, water and red oil exits reactors 11 through line 14 and enters into acid settlers 15. The settlers operate at a controlled interface allowing converted hydrocarbons to exit through overhead line 18. Some acid is recycled through line 22 while the rest is routed to the next reactor through line 13. Acid exits the final reactor/settler and is sent to a final acid settler 30 through line 16 where remaining hydrocarbons are separated and removed through line 19. The spent acid is then sent through line 20 into holding tank 21.

The recycle acid in line 22 is comprised of water, mineral acid and acid-soluble hydrocarbons, i.e., red oil. The water content is typically from about 1 to about 9 weight percent, more usually from about 3 to about 5 weight percent. The mineral acid concentration is typically from about 89 to about 98 weight percent, more usually from about 92 to about 95 weight percent. The acid-soluble hydrocarbon concentration is typically from about 5 to about 10 weight percent, more usually from about 5 to about 7 weight percent.

Fresh acid at typically 98 weight percent enters through line 26 and control valve 27 where it mixes with line 22 recycle acid and enters the reactor through line 17. The amount of acid entering line from 26 is such as to maintain the acid strength in the alkylation reactors, preferably dropping in strength across the reactors and finally exiting at 89 weight percent.

At least one sensor 3a is placed in the spent acid line 16 to the final acid settler 30. Additional sensors 3b can be placed in the acid recycle lines 22. The sensors produce a signal relating to acid strength which is sent to at least one transmitter 24 and is converted via a processor 25, such as a central processing unit ("CPU"), using the appropriate computer program which is calibrated to convert refractive index units into weight percent. As set forth in FIG. 1, the most desirable place for the sensor is in the spent acid line 16 just prior to the final acid settler 30. Additional sensors can be placed in the recycle acid line before it is mixed with fresh acid. The sensor 3a and the transmitter 24 will be discussed in greater detail herein.

The acid concentrations obtained from sensor 3a and 3b and flow rates on lines 17, 26, and 13 are fed to a distributed control system (DCS) 28 which operates control valves 27 and 23 to allow sufficient fresh acid to enter line 17. This is done so that the mixed recycle/fresh acid has the desired concentration at predetermined flow rates entering reactor 11.

There are three primary acid streams shown in FIG. 1, lines 10, 16, and 22, which are preferred for monitoring acid strength in the system, although it will be recognized by one skilled in the art of refinery alkylation processes that many alternative monitoring locations are possible. It is preferred in the practice of the invention that the acid stream be a substantially homogenous stream, i.e., substantially free of droplets or bubbles.

A preferred location for one of the sensors 3a is shown in FIG. 1. The inclusion of a temperature sensor within each analyzer sensor 3 will be discussed in greater detail herein. A temperature correction may be used later in the data analysis to correct the refractive index.

Figure 2:
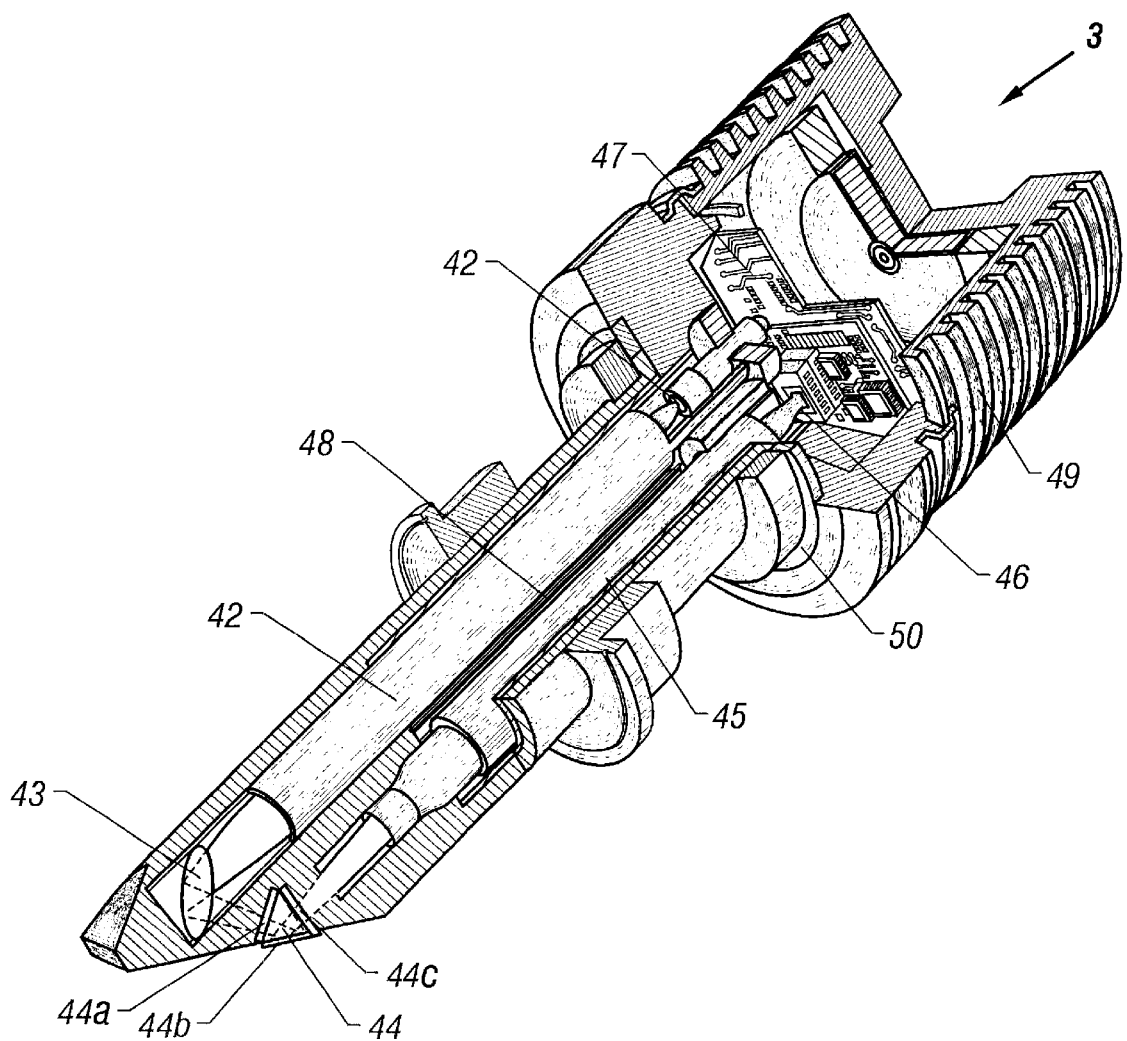
FIG. 2 is a cross-sectional view of the sensor assembly including refractor prism suitable for use within the method of the invention.

A refractor prism is preferable for use in the analyzer sensor 3. An embodiment of this prism 44 is shown in FIG. 2. The sensor 3 is displayed in cutout perspective to allow some of the internal components to be better depicted. As shown, a light source 42, preferably a light-emitting diode (LED), emits a beam of light that may be channeled via fiber-optic 42 or similar optical transmission conduit such that the exiting light may be reflected by at least one mirror 43 and enter a prism 44 from an entrance surface 44a of the prism 44. At least a portion of the light will be reflected off of the measuring surface 44b, as will be discussed in greater detail herein, and exit the prism 44 via the exit surface 44c. Fiber-optic 45 or a similar optical transmission conduit may channel this light to an image detector 46. Additionally, those skilled in the art will recognize that inclusion of condenser optics before or after either fiber optic 42 or fiber optic 45 may be useful. The image detector 46 preferably includes a multi-segment charge-coupled device ("CCD"). Those skilled in the art will recognize that the image detector 46 may be linked to an image digitizer 47 contained within the sensor 3. This arrangement allows for the creation, processing and ultimately, transmission of digital information that is not subject to the drifting effect found in analog to digital conversion arrangements. Those skilled in the art will recognize that a temperature sensor 48 may be disposed within sensor 3 to collect temperature measurements. The collection of temperature information may also be processed such that the correlation between the temperature and the information collected by image detector 46 and analyzed by image digitizer 47 may be calibrated to account for any change in the refractive index because of temperature variations. Additionally, sensor 3 may include air-cooling surfaces 49 to allow the dissipation of heat accumulated during use. Moreover, thermal isolation 50 encourages accurate and precise measurements while lengthening the useful life of the components that are insulated such as the image detector 46 and image digitizer 47.

An example of a preferable sensor, for this purpose is the K-Patents Process Refractometer™ PR-01-S-K. It can determine the refractive index of the process solution by measuring the critical angle of refraction, $\Phi_{CRIT}$, which changes with concentration and temperature. In this preferred embodiment, the critical angle $\Phi_{CRIT}$ is measured by a CCD-scanner, the image detector 46 in this configuration, situated within a rugged steel probe assembly of the sensor 3.

This configuration prevents the color of the solution, gas bubbles, or undissolved particles from affecting the measurement result. Because the image digitizer 47 is incorporated within sensor 3, the sensor 3 remains calibrated to a desired range and there is no need for corrections of the calibration. This optical image detection system prevents signal drift associated with analog devices. Additionally, the incorporated microprocessor signal linearization and temperature compensation allows for absolute calibration in concentration units. The inclusion of fiber optics 42 and 45 allow for the light source 42 and image detector 46, respectively, to be located in ambient temperature-away from the hot process and this significantly reduces the need for regular maintenance. This refractometer sensor 43 uses an optical image detection algorithm to locate the shadow line with higher precision and reliability than the fixed threshold method.

Figure 3:
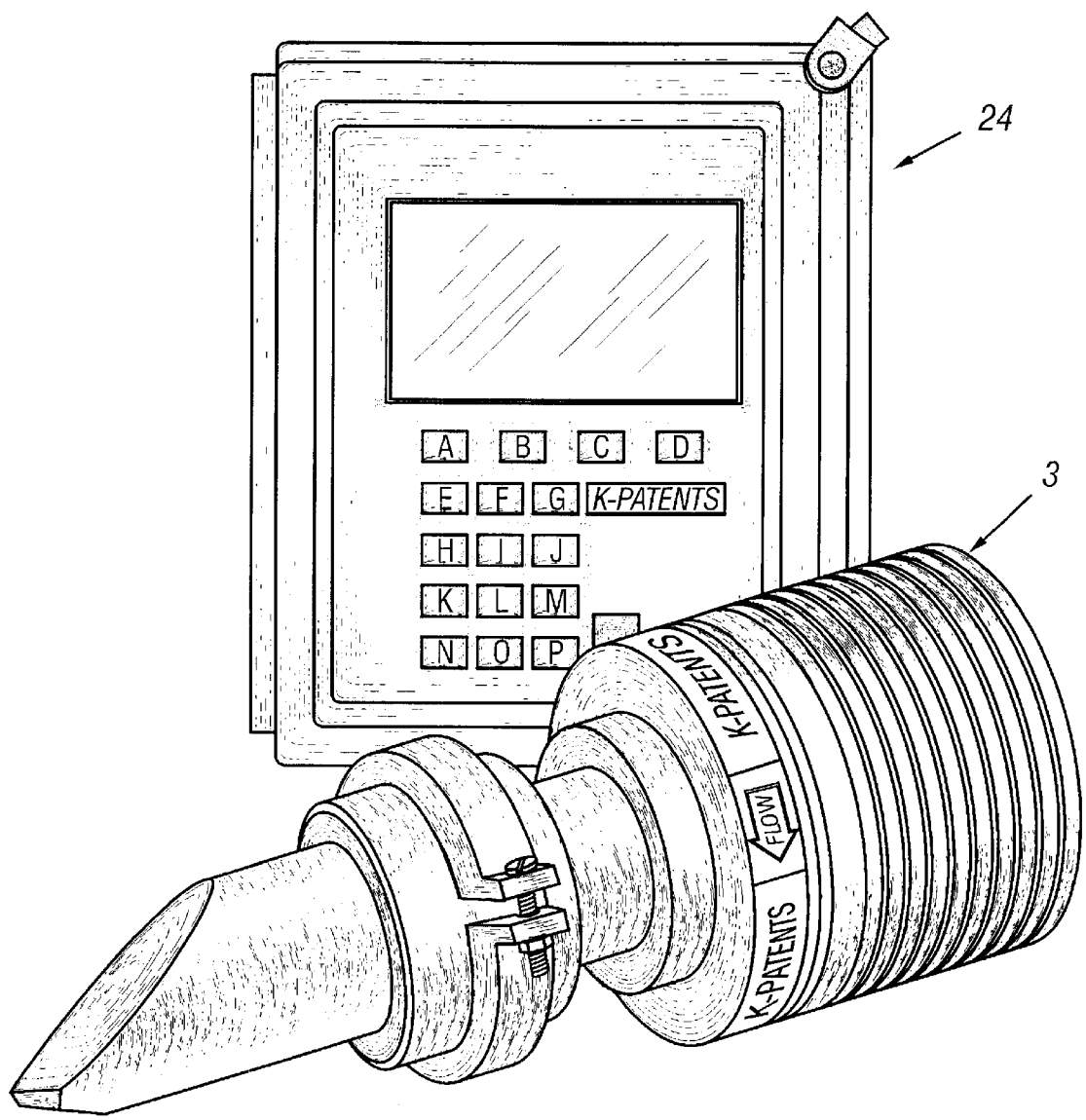
FIG. 3 illustrates the sensor and indicating transmitter of the refractive index analyzer suitable for use within the method of the invention.

The use of a separated sensor 3 and indicating transmitter 24 as shown in FIG. 3, provides for better placement and safety concerns. Therefore each sensor 3 may be placed such that it provides optimum flow velocity conditions on the measurement surface 44b of each prism 44 keeping it automatically clean. The sensor 3 is preferably capable of the following:

TABLE 1

Sensor Range

| Range | Refractive Index (nm) |
|---|---|
| Low or Standard | 1.320–1.460 |
| High | 1.380–1.530 |
| Very High | 1.470–1.630 |

In the preferred configuration, at least one sensor 3 is connected as shown in FIG. 1. In this Figure, sensor 3 is connected to indicating transmitter 24 via line 34 such that it may pass through a barrier or a similar safety structure. This allows for the sensor to be placed in an environment wherein possibly hazardous conditions may exist. Workers viewing the indicating transmitter 24 may be safely disposed on the opposite side of the barrier. Additionally, FIG. 1 shows sensor 3a and additional sensor 3b disposed for monitoring the acid strength. Those skilled in the art will realize the advantages of being able to monitor the concentration at different locations. For example, the sensors 3 may notify or be used to activate the altering of the feed concentration of acid such that the exit concentration of acid is greater than about 86% by weight concentration, preferably about 89% by weight concentration. This real-time fashion allows the monitoring and even automatic adjustment to desired concentration levels.

Transmitter 24 may also connect via line 35 to a valve actuator such that valves 23 or 27 may be automatically or manually opened or closed to control the addition of more acid via line 26. Those skilled in the art will recognize that an alarm or similar attention device may be installed that is activated if the concentration level of a constituent in the stream passing about sensor 3 exceeds or falls below a predetermined level. Effectively, a dynamic adjustment of the constituent in the solution is possible by increasing the acid supply feed 26 in the preferred embodiment. This automatic adjustment of this constituent concentration improves efficiency while providing safety to workers by distancing the human interaction with the system. Sensors 3a, 3b, and any additional sensors may be similarly connected such that the concentration streams may be monitored on a real-time basis and contemporaneous adjustments may be automatically or manually made accordingly.

As shown herein, each sensor 3 may preferably provide a current output of 4–20 mA/0–20 mA, max load 1000 Ohm with a galvanic isolation 1500 V DC or AC (with a peak). Moreover, the connections may utilize any wire or electrical conduit. The use of at least one serial RS485/RS232 in the present invention is preferred. These connections may have a galvanic isolation of 500V DC or AC (peak).

Additionally, the light source is preferably an infrared (GaAs) emitting diode with a narrow spectral emission peak at 930 nm which can be considered as nearly monochromatic. The use of monochromatic light avoids non-linear effects created by a band of frequencies. Those skilled in the art will recognize that additional sources of substantially monochromatic light such as laser diodes are within the scope of this invention. The light source 42, preferably has a broad Gaussian beam (approx. ±20°) dispersion so that a portion of the light emitted from the light source 42 is refracted on the measuring surface 44b.

Figure 4:
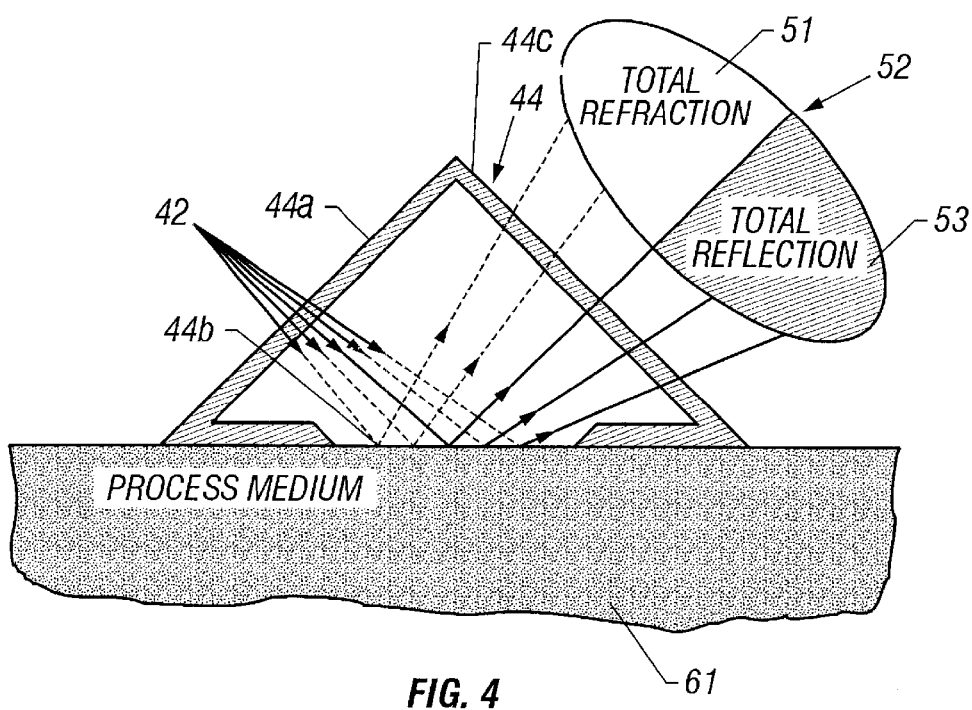
FIG. 4 illustrates refracted and reflected light rays using the refractive index analyzer in accordance with the method of the invention.

As shown in FIG. 4, the portions of the light rays that are at angles larger than the critical angle $\Phi_{CRIT}$ are reflected by the measuring surface 44b towards the image detector 46 (not shown in this figure). Light rays incident on measuring surface 44b at angles smaller that the critical angle $\Phi_{CRIT}$ refract in the process medium 61 in contact with measuring surface 44b and are not reflected.

Basically, this narrow bandwidth beam is emitted by light source 42 and is directed onto measuring surface 44b where some of the beam that is larger the critical angle $\Phi_{CRIT}$ will be reflected back by surface 44b and to total reflection area 53. Light rays that arrive at an angle to measuring surface 44b that are equal to or smaller than the critical angle $\Phi_{CRIT}$ will be refracted out the prism 44 via exit surface 44c to total refraction area 51. The beams reflected back to the base by measuring surface 44b can be detected by detector 46 and the critical angle determined by the amount of light detected by detector 46.

The critical angle $\Phi_{CRIT}$ will be dependent on the refractive index of the prism 44 and on the refractive index of material in contact with measuring surface 44b. Therefore, the refractive index of a liquid in contact with measuring surface 44b can be determined from the light detected by detector 46 by finding the critical area of the transition point 52. Due to the small change in refractive index of various solutions introduced during operation of the present invention, the change in position of the boundary between refracted 53 and reflected rays 51 is also very small.

As for the optical detector, the use of image detector 46 and image digitizer 47 will find the bright-dark boundary that is the transition point 52 using the linear interpolation, polynomial-curve interpolation, or fitting method. The term "bright-dark boundary" or transition point 52 as used herein means the boundary between a region of total light reflection 51 and a region of total refraction 53. Along the bright-dark boundary or transition point 52, the Fresnel diffraction phenomenon occurs. In determining the bright-dark boundary, it is convenient to exploit the Fresnel diffraction phenomenon in which the quantity of light of the measured waveform is always increased beyond that of the reference light. The point of intersection closest to the portion where the light quantity has increased between the reference waveform and the measured waveform is read out as the bright-dark boundary or transition point 52.

Figure 5:
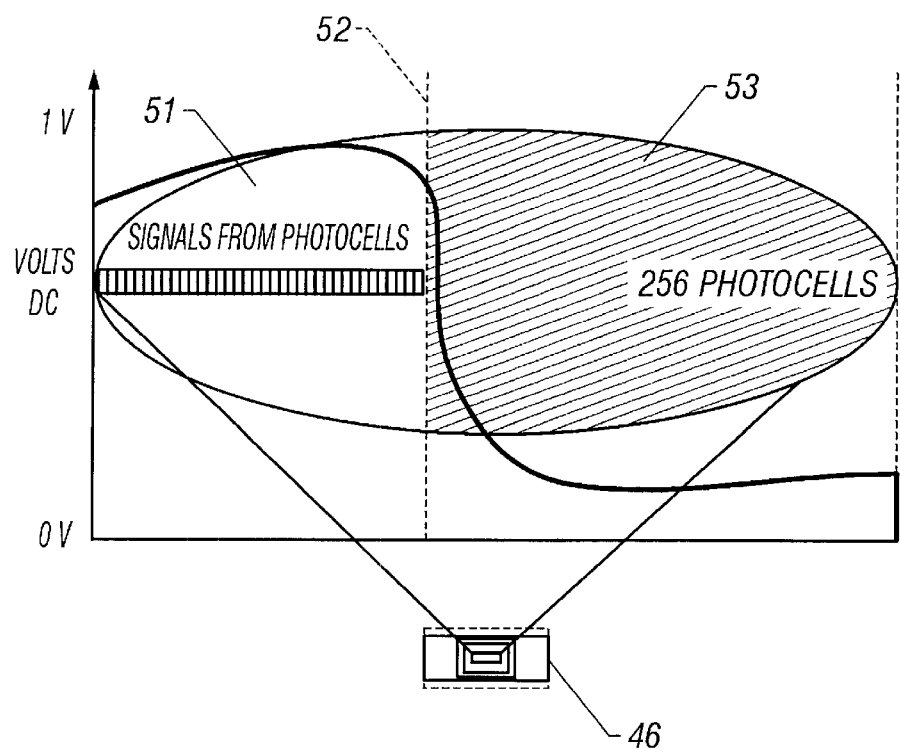
FIG. 5 illustrates the image detector capturing the light rays within the refractive index analyzer in accordance with the method of the invention.

Referring to FIG. 5, the image detector 46 captures the light, that is in turn processed by image digitizer 47, to form voltage signals from the photocells can be divided into the three regions. These regions relate to the total refraction region 51, the total reflection region 53 and the transition point or bright-dark boundary 52. The image digitizer locates the region 52 by noting the voltage shift from nearly about one-volt in the preferred embodiment to significantly less as shown herein.

Figure 6:
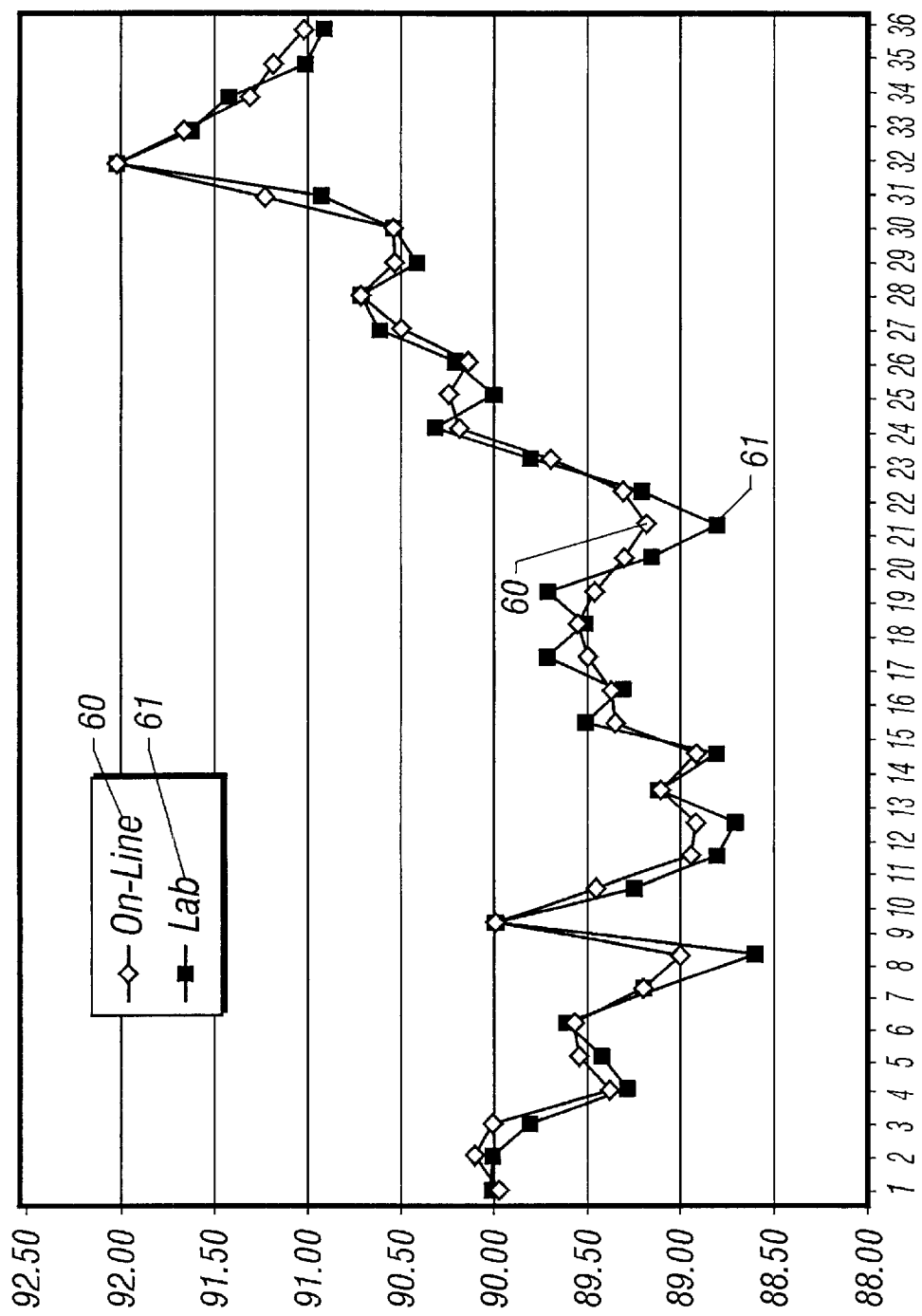
FIG. 6 illustrates the achievement of a precise calibration of the on-line refractive index analyzer used in the method of the invention.

The on-line analyzer system using the sensor 3 and transmitter 24 were calibrated shown by the graph displayed in FIG. 6. As shown, the weight percentage concentrations found display with respect to the Y-axis are mapped shown intervals 1–36 along the X-axis. During this process, the real-time, online signals 60 were compared to manual samples taken and analyzed in a lab setting 61. The graph shows the correlation of concentrations and calibration of the instrument to provide precise real time reflection of the concentration within the stream as compared to the lab results.

Figure 7:
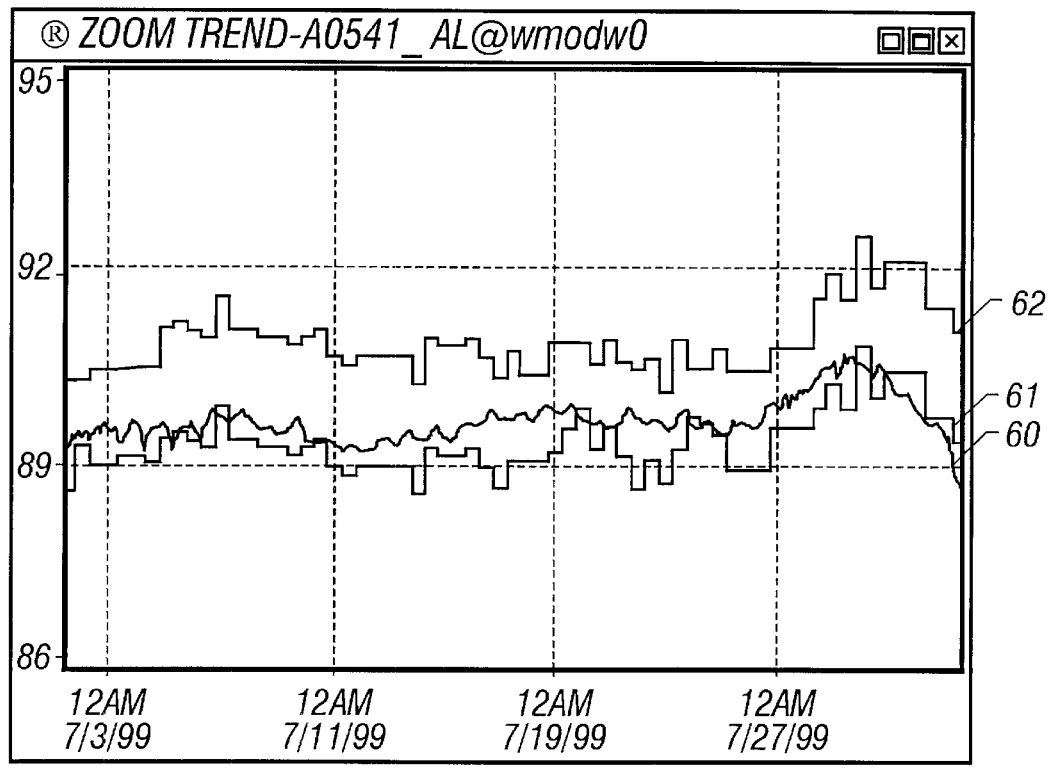
FIGS. 7 and 8 depict reactor runs under the method of the invention using the refractive index analyzer compared to the results of periodic, manual lab testing procedures.
Figure 8:
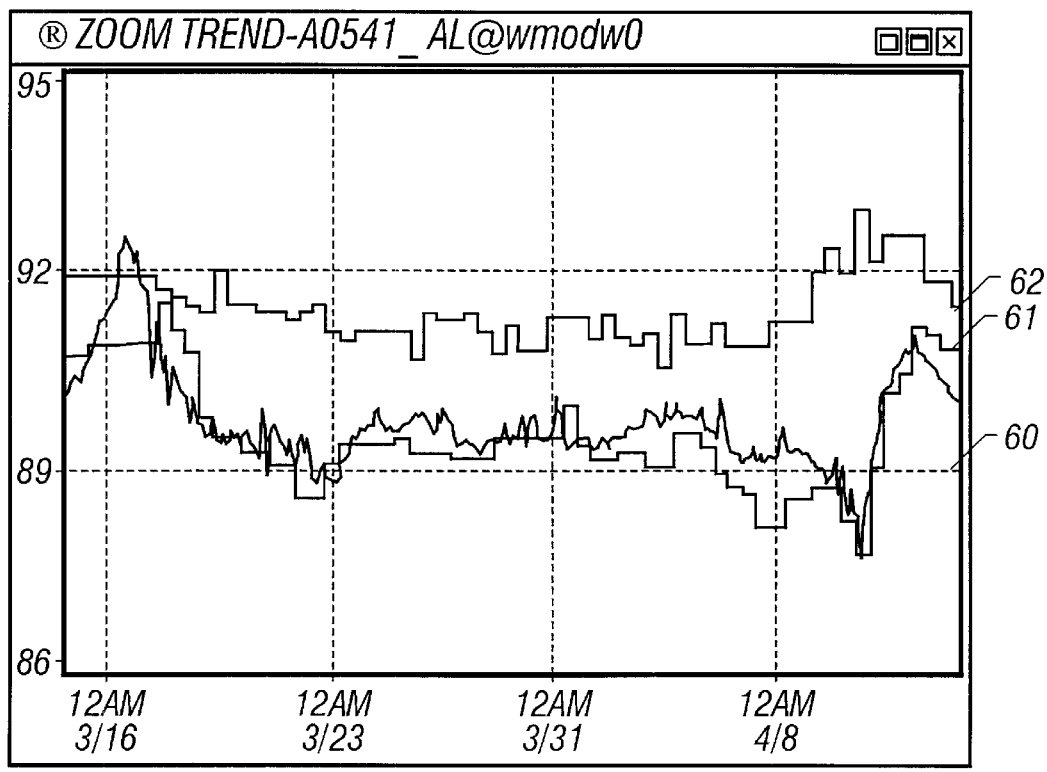

Using this calibration, FIGS. 7 and 8 show reactor runs wherein the real-time, on-line analyzer system was compared to the results of periodic, manual lab testing procedures. The incoming stream is shown by line 62 on each graph. Accordingly, the concentration taken by the on-line analyzer system using at least one sensor and at least one transmitter is shown by line 60. To compare these results, the manual samples taken are shown by line 61 in both graphs. As shown, the concentration levels shown by lines 60 and 61 follow one another and confirm that the on-line analyzer provides precise enough information related to the concentration of the constituent in the solution such that real-time analysis of the concentration may be performed using the on-line analyzer system as depicted herein. Accordingly, the remote verification of the concentration levels allows real-time adjustment of the effluent streams and the introduction of additional catalyst, if necessary, in order to maintain concentration levels such that an efficient and cost effective stream may be maintained. Accordingly, by utilizing the system as described herein, those skilled in the art will recognize that these advantages may be maintained while offering a greater degree of safety and care of the workers operating within the facilities.

While the illustrative embodiments of the invention have been described with particularity, it will be understood that various other modifications will be apparent to and can be readily made by those skilled in the art without departing from the spirit and scope of the invention. Such variations and modifications are within the scope of the described invention and the appended claims.

Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled the art to which this invention pertains.

What is claimed is:

1. In a method for determining the concentration of acid in a solution containing unkown quantities of said acid within an alkylation reactor, the method comprising forming a solution containing said acid in said alkylation reactor and measuring the concentration of said acid, the improvement comprising measuring the concentration of said acid within the said alkylation reactor with a refractive index sensor having: (a) a refracting prism with a measuring surface in contact with the solution; and (b) an image detector capable of producing a digital signal related to the refractive index of the solution by determining a bright-dark boundary between reflected and refracted light from the measuring surface and correlating the refractive index of the solution to the concentration of said acid in said solution.

2. The method of claim 1, wherein the acid is selected from the group consisting of sulfuric acid and hydrofluoric acid.

3. The method of claim 1, wherein the solution is a mixture of mineral acid, water and acid-soluble hydrocarbon.

4. The method of claim 3, wherein the acid-soluble hydrocarbon is red oil.

5. A method for controlling the acid strength in an alkylation reactor comprising:

(a) forming within the alkylation reactor a reaction mixture by contacting an olefinic feedstream with an acid catalyst for a time sufficient to convert the feed stream into reaction product;

(b) ascertaining an acid strength reading of the acid catalyst in the alkylation reactor by a refractive index analyzer which measures the refractive index of the reaction mixture and correlates the refractive index to the acid strength; and (c) adjusting, when necessary, the concentration of acidic catalyst within a predetermined range by adding acid to the alkylation reactor.

6. The method of claim 5, wherein the concentration of acid catalyst in step (a) is between about 89 to about 98 weight percent.

7. The method of claim 6, wherein the concentration of acid in step (a) is about 98% weight strength.

8. The method of claim 5, further comprising continuously monitoring the acid strength with the refractive index analyzer.

9. The method of claim 5, wherein the acid catalyst is selected from the group consisting of sulfuric acid and hydrofluoric acid.

10. The method of claim 5, wherein the reaction product in step (b) comprises mineral acid, water and acid-soluble hydrocarbon.

11. The method of claim 10, wherein the acid-soluble hydrocarbon is red oil.

12. The method of claim 5, wherein the predetermined range is between from about 89 to about 98 weight percent.

13. The method of claim 12, wherein the predetermined range is between from about 92 to about 98 weight percent.

14. The method of claim 13, wherein the predetermined range is about 98 weight percent.

15. The method of claim 5, wherein the temperature in the alkylation reactor is from about −60° F. to about 1000° F.

16. The method of claim 15, wherein the temperature in the alkylation reactor is from about −40° F. to about 200° F.

17. The method of claim 16, wherein the temperature in the alkylation reactor is from about 35° F. to about 200° F.

18. The method of claim 15, wherein the pressure in the alkylation reactor is from about 45 PSI to about 1000 PSI.

19. The method of claim 18, wherein the pressure in the alkylation reactor is from about 45 PSI to about 250 PSI.

20. In a method for monitoring and controlling the acid strength in an alkylation reactor, the method comprising forming a reaction mixture containing an acid catalyst and an olefinic feed stream in said alkylation reactor and measuring the acid strength of said reaction mixture, the improvement comprising determining the acid strength of acid catalyst in the alkylation reactor by a refractive index analyzer, which measures the refractive index of the reaction mixture and correlates the refractive index to the acid strength and adjusting acid, when necessary, the concentration of acid catalyst within a predetermined range by adding fresh acid to the alkylation reactor.

* * * * *

UNITED STATES PATENT AND TRADEMARK OFFICE
CERTIFICATE OF CORRECTION

PATENT NO.     : 6,387,705 B1
DATED          : May 14, 2002
INVENTOR(S)    : Terry V. Claibourn and Phillip J. Hamilton It is certified that error appears in the above-identified patent and that said Letters Patent is hereby corrected as shown below:

Column 12,
Line 43, delete "acid".

Signed and Sealed this

Twenty-fourth Day of June, 2003

JAMES E. ROGAN
*Director of the United States Patent and Trademark Office*